United States Patent [19]

Kawamura et al.

[11] Patent Number: 5,308,757
[45] Date of Patent: May 3, 1994

[54] BIOLOGICAL CELL TREATMENT METHOD AND APPARATUS

[75] Inventors: Yoshio Kawamura, Kokubunji; Yoshu Yoshiba, Ageo; Shinji Tanaka, Akishima; Kazuo Sato, Tokyo; Jiro Kikuchi, Yuki; Kahoru Takahashi, Katsuta, all of Japan

[73] Assignees: Hitachi, Ltd.; Hitachi Koki Co., Ltd., Tokyo, Japan

[21] Appl. No.: 742,419

[22] Filed: Aug. 8, 1991

[30] Foreign Application Priority Data

Aug. 8, 1990 [JP] Japan .................. 2-208110

[51] Int. Cl.⁵ .................. C12Q 1/02; C12N 5/00; C12M 1/00; C12M 1/20
[52] U.S. Cl. .................. 435/29; 435/240.1; 435/240.2; 435/240.4; 435/284; 435/287; 435/291; 435/300; 435/301; 935/89; 935/94; 935/98; 436/63; 436/807; 436/809
[58] Field of Search .................. 435/29, 286, 287, 284, 435/300, 301, 240.1, 240.4, 240.2, 291; 436/63, 807, 809; 935/89, 94, 95, 98

[56] References Cited

U.S. PATENT DOCUMENTS

| | | |
|---|---|---|
| 4,476,225 | 10/1984 | Grigorian et al. .................. 435/287 |
| 4,729,949 | 3/1988 | Weinreb .................. 435/291 |
| 4,760,020 | 7/1988 | Neufeld .................. 435/29 |
| 4,894,343 | 1/1990 | Tanaka et al. .................. 435/301 |
| 4,895,805 | 1/1990 | Sato et al. .................. 435/286 |

OTHER PUBLICATIONS

Sensors & Actuators, A21-A23, 1990, "Individual and Mass Operation of Biological Cells Using Micromechanical Silicon Devices", Sato et al, pp. 948-953.
Journal of Japan Society for Precision Engineering, 56, 1990, "Development of One-to-One Biological Cell Fusion Technique Using Micromechanical Devices", Kawamura et al, pp. 86-91.

Primary Examiner—Michael G. Wityshyn
Assistant Examiner—Jane Williams
Attorney, Agent, or Firm—Fay, Sharpe, Beall, Fagan, Minnich & McKee

[57] ABSTRACT

In determining the effectiveness of parameters on cells, after treatment of the cells with one or more selected parameters, the results of the treatment can be quickly determined by measuring the number $n_0$ of cells having a predetermined cell form, subsequently mechanically stressing the cells for a sufficient period of time t to change the cell form substantially, thereafter again measuring the number n of cells having the predetermined cell form, and determining the cell viability $\tau$ defined by $\tau = t/\ln(n_0/n)$.

42 Claims, 4 Drawing Sheets

BIOLOGICAL CELL TREATMENT METHOD AND APPARATUS

BACKGROUND OF THE INVENTION

This invention relates to biological cell treatment, and more particularly to evaluating the biological viability or survivability of cells.

In order to prevent the cells supplied to a microchamber from individually adhering to the surfaces of the walls of the microchambers, a hydrostatic pressure is applied intermittently (in an amount and manner similar to that of the present invention) from apertures in the bottom portions of the chambers to the interior thereof as disclosed in Japanese Patent Laid-Open No. 95768/1989 and U.S. patent application Ser. No. 07/253,560 filed October, 1988 now U.S. Pat. No. 5,154,814.

In general, the protoplast used for the cell fusion of a plant is protoplasm obtained by isolating leaf cells by enzyme treatment to remove the cell walls. As disclosed in the literature (edited by an incorporated body of the Technical Information Association of Agriculture, Forestry and Fisheries, "Research Journal", Vol. 13, No. 5, (1990-5) 3-12), fused hybrid cells are transferred onto a culture medium, and the cell walls are subjected to regeneration, cell division and callusing, the hybrid cells then growing into a plant body. The protoplast isolating condition differs according to the kind of plant, and it is said to be important to develop an optimum protoplast isolating condition under which the viability of protoplast, i.e. the capability of regenerating, dividing and multiplying the cell walls thereof, is not spoiled.

The treatment condition including optimum isolation, culture and cell fusion has been researched by trial and error repeatedly, usually by transferring protoplast pretreated with various kinds of cell wall digesting enzymes (such as pectinase and cellulase) onto a culture medium, culturing the same for several weeks, and observing the condition of the protoplast being divided and multiplied, or by cultivating this protoplast for more several months and observing whether an original plant body is regenerated or not. Such conventional determining of viability involves a technical problem that it takes at least 2-3 weeks before the viability results have been obtained. Moreover, it is necessary that the protoplast be put under an aseptic condition to be cultured for a long period of time. Consequently in determining viability, a great deal of labor is required in enzyme treatment, to make sterilization arrangements and to control the sterilization of a culture medium for a long period of time.

SUMMARY

According to the above-described conventional techniques, the time required to research the protoplast isolating condition cannot be reduced, and these techniques have a problem that researching such an isolation condition takes at least 2-3 weeks before the results have been obtained.

An object of the present invention is to provide, in a short period of time, the establishment of an optimum condition of a cell, particularly for isolating protoplast, particularly of cells of a plant or an animal, and to provide a body, particularly an animal or plant body of a stable quality by regenerating and selecting only such cells that have a high viability and survivability.

When the cells are animal, the present invention can solve pathological problems relating to finding an antibody and medicine capable of lowering the activity of malignant tumor cells, or an antibody and medicine capable of promoting the regenerative viability of cells.

To achieve these objects and as a part of the present invention, the inventors have obtained knowledge from the results of experiments conducted by the inventors.

The protoplast isolated by treating a plant body with an enzyme is influenced by treatment liquid and the protoplast is apt to lose its viability, i.e. the capability of regenerating the cell walls and dividing and multiplying the same. Namely, the viability or survivability of the protoplast lowers with conventional enzyme treatment over time.

It has been discovered from the results of the inventor's experiments that, when mechanical stress is loaded on cells, the influence which a treatment exerts upon the cell membranes and protoplast during a treatment can be made clear and accurate in a shorter time than that conventionally required and without such strict sterilization requirements conventionally required. The influence of a treatment upon the viability of cells can be determined clearly and accurately as a change in the form of the cells and, especially, as a difference in the rate of damage to the cells. Namely, it has become clear that the viability of cells quickly can be made clear and determined accurately by loading sufficient mechanical stress on the cells.

The present invention has solved the above-mentioned problems by a preferred embodiment, including the inventor's analysis and experiments.

When protoplast receives sufficient mechanical stress, such as from a suction force, the number of cells that vary in form with the lapse of time increases, especially, the number of cells broken under this condition increases. Accordingly, treating a large quantity of protoplast under the same conditions and loading mechanical stress thereon enables the change with time of individual cell forms to be recognized quickly, and thereby the viability of the protoplast can be quantitatively and quickly determined. When mechanical stress is loaded on the cells, the variation of the viability thereof can be made clear and accurate in a short period of time, so that the quantitative determination of the viability of protoplast can be done in a short period of time. Moreover, since determining the condition for setting the cells to be observed in a desired state can be done easily, cells of a stable quality can be selected, and multiplied cells based thereon can be produced with a high efficiency.

BRIEF DESCRIPTION OF THE DRAWING

Further objects, features and advantages will become more clear from the following detailed description of the drawing, wherein.

DETAILED DESCRIPTION OF THE DRAWINGS

A biological cell fusion apparatus shown in Yoshio Kawamura et al, "Development of One-to-One Biological Cell Fusion Technique Using Micromechanical Devices", Journal of Japan Society for Precision Engineering, 56, 1(1990)86–91) [also printed in Sensors and Actuators A21–A23 (1990) 948–953 under the title "Individual and Mass Operation of Biological Cells Using Micromechanical Silicon Devices", and disclosed in U.S. Pat. Nos. 4,895,805 and 4,894,343, the disclosure of which U.S. patents is incorporated herein by reference] has been developed by the present inventors. In this apparatus, a large quantity of cells are handled and operated upon to be supplied individually and simultaneously to a chamber, which has about 1600 minute chambers.

An embodiment of the present invention will now be described with reference to FIG. 1. The reference numerals common to FIG. 1 and other drawings represent parts of the same function.

Figure 1:
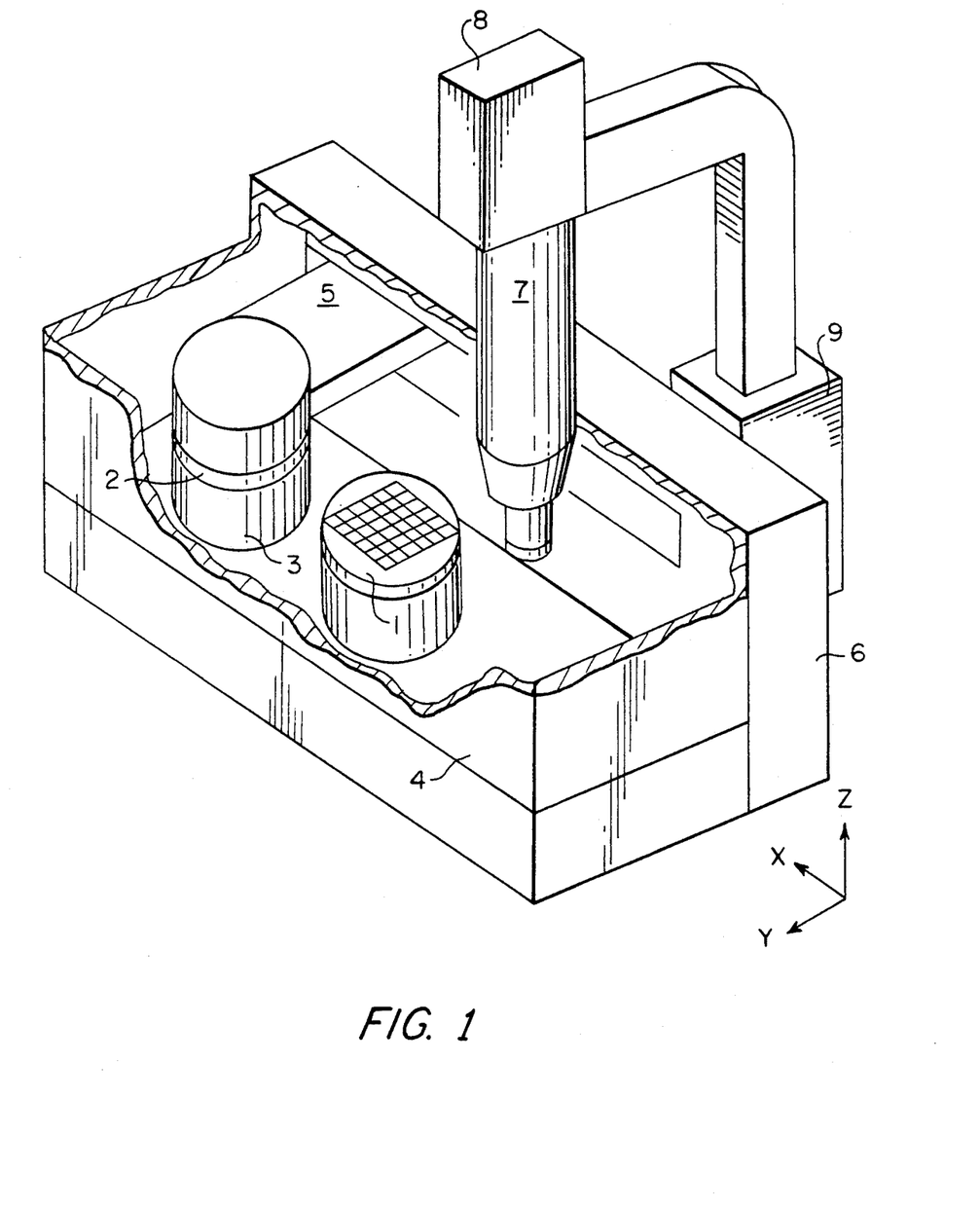
FIG. 1 shows the measuring apparatus according to the present invention.
Figure 2:
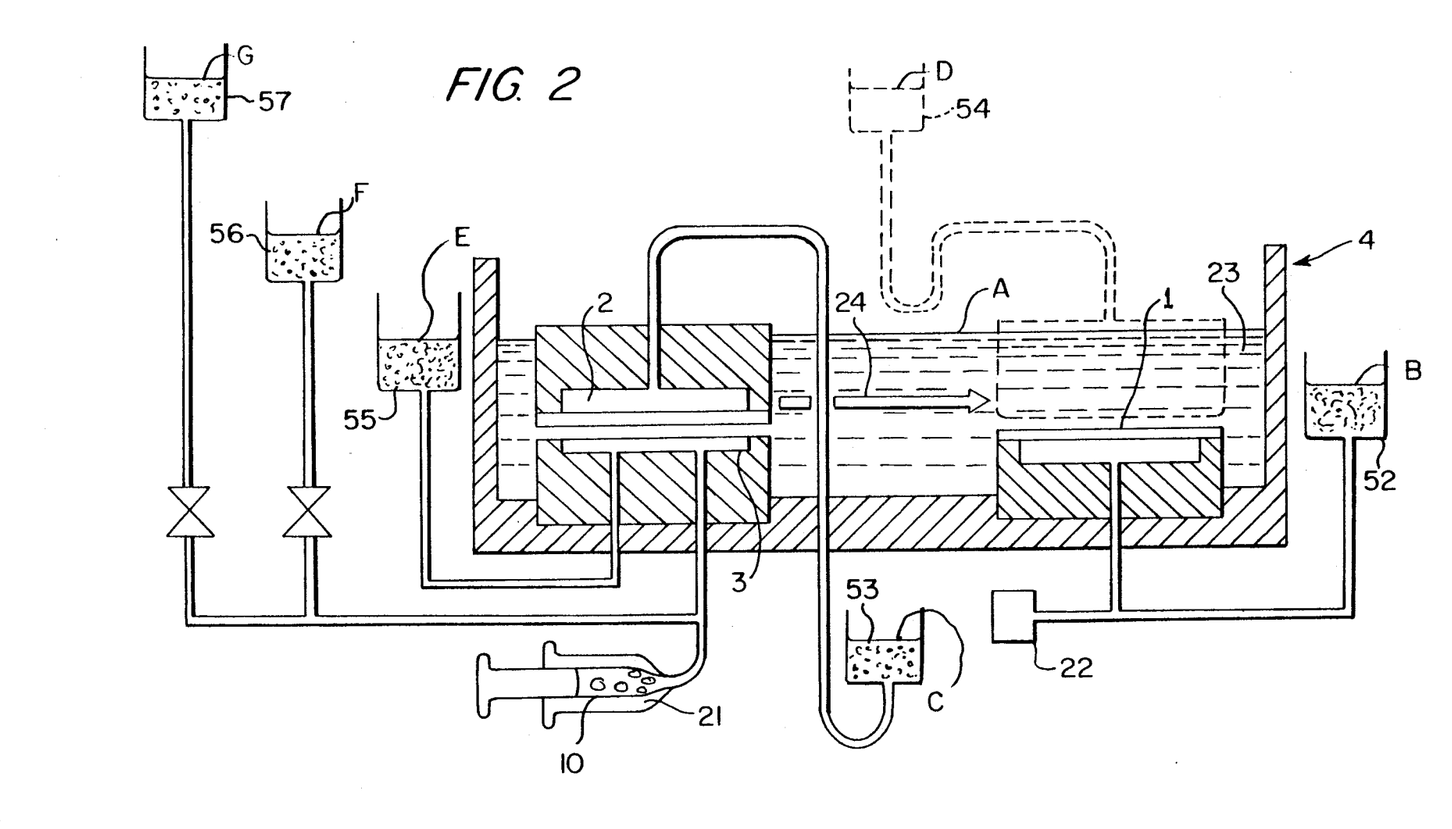
FIG. 2 is a sectional view of a main mechanism in the measuring apparatus

An embodiment of the present invention is shown in FIG. 1 with a top portion of a vessel 4 broken away to show the interior structure in FIG. 2. An example where protoplast of plant cells is used as cells 10 to be observed will be described.

This embodiment has a microchamber plate 1 composed of a large plurality, for example about 1600, of matrix arrayed microchambers in each of which a single protoplast cell is kept and stored, and a carrier plate 2 which is handling means for absorbing a large quantity of protoplast contained in an injector 21 for transferring the protoplast individually to a respective microchamber and simultaneously injecting the same into all of the microchambers of plate 1.

More specifically, a matrix array of 1600 microchambers, each for containing a single cell, has been fabricated on a 3 inch silicon wafer. The carrier plate has the same numbers of cell absorption ports in the matrix array as the microchambers. The protoplast of a single cell is absorbed too and released from each port by applying negative and positive liquid pressure from the rear side of the carrier plate 2 respectively. The carrier plate 2 is then transferred by carriage 5 from its illustrated position to be transferred over the microchamber plate 1 and thereafter simultaneously releases cells individually from the ports into the microchambers.

A supply pool 3 supplies the protoplast from the injector 21 to the carrier plate 2. The vessel 4 is filled with an isotonic solution 23 used to provide the protoplast with an osmotic pressure maintained at a predetermined level. Carriage 5 transfers the protoplast-absorbed carrier plate 2 from the supply pool 3 to the microchamber plate 1 in the direction of an arrow 24 within the isotonic solution 23 in the vessel 4.

A control system 6 controls a sequence of operations including the supplying of protoplast to the pool 3, the sucking of protoplast from the pool 3 into the carrier plate 2, the carrying of the carrier plate 2 in the direction of arrow 24, the pouring of protoplast from plate 2 into the microchamber plate 1 and the keeping of the protoplast in the microchambers of the microchamber plate 1.

Figure 3:
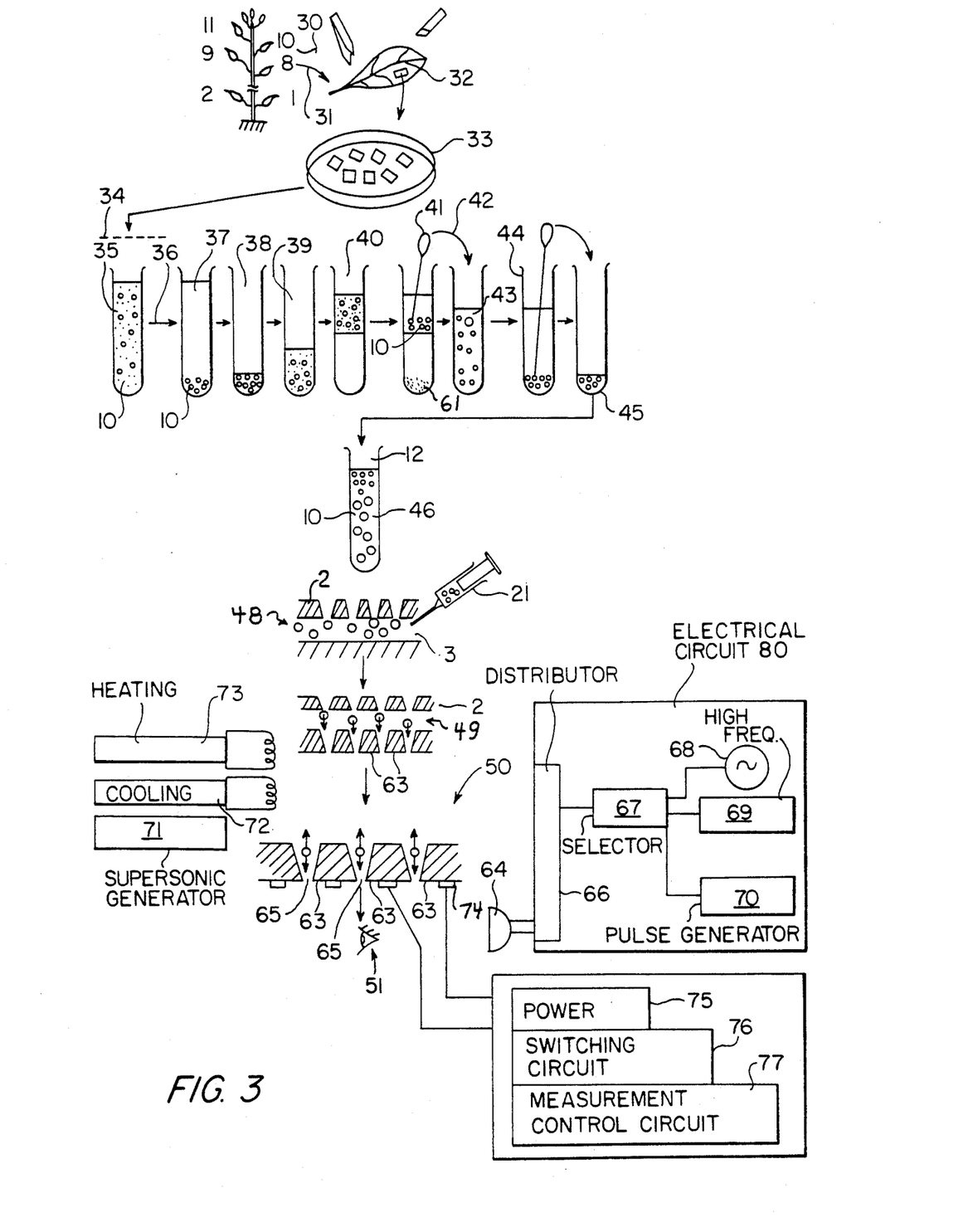
FIG. 3 is a diagram showing the procedures in operating the apparatus of FIGS. 1 and 2, according to the present invention.

The above mentioned cell-delivery sequence to the microchamber is specifically illustrated in FIG. 2 and in FIG. 3. In step 48, the protoplast is introduced into the supply pool 3 by the injector 21. The carrier plate 2 faces downwardly with respect to a flat plate that defines the bottom of the pool 3. Cells of a kind of group are fed to the pool 3 and suspended in isotonic solution in the supply pool 3. When a small amount of suction is applied above the carrier plate 2, the protoplast will be absorbed to the ports on the carrier plate 2. The carrier plate 2 is provided with a matrix of such ports that is identical in number to and in the identical position as that of the microchambers of plate 1. Therefore, a single cell is absorbed to each port of the carrier plate 2, after which the carrier plate 2 is transferred in the direction of arrow 24 of FIG. 2 to be in full alignment over the microchamber plate 1 as shown for step 49 in FIG. 3. Thereby, the absorption ports on the carrier plate 2 align with the microchambers face-to-face. When the topside of the carrier plate 2 is pressurized, the absorbed cells are simultaneously released from the carrier plate 2 and fall into the chambers of the microchamber plate 1. Thereafter, a single cell can be found in each of the microchambers of the microchamber plate 1. An optical microscope 7 is for use in observing the protoplast in the microchambers on a 40×40 matrix type arrangement through the top of the vessel 4. A camera 8 is connected to the optical microscope 7. A stage 9 moves these optical systems 7, 8 relative to each other in the x and y directions.

The term cell as used herein refers to both a complete cell before enzyme treatment to remove the cell wall to leave protoplast and to the protoplast that has no cell wall.

In step 50, the protoplast floats upward a small distance from the bottom slits 65 of each microchamber for each of several-second time intervals due to operation of a pressure oscillator 22 adapted to pressurize the protoplasts 10 intermittently. Therefore the pressure oscillation frequency can be about 4 to 15 cycles per minute. The protoplast supplying and sucking pressures are expressed, monitored and maintained in terms of water heads B–G in siphons 52–57 used for this purpose. The water heads in this embodiment, which are determined relative to the water head A in the vessel 4, are B=−4 mm Aq, C=−5 mm Aq, D=10 mm Aq, E=−5 mm Aq, F=10 mm Aq and G=28 mm Aq, where 10,000 mm Aq=1 Kg/cm$^2$.

FIG. 3 is effectively a schematic flowchart and shows an example of the operation of the above-described apparatus for an isolation treatment for protoplast, according to the present invention for determining the viability/survivability of cells.

According to step 30, a plant having plurality of leaves on it is examined to determine the age of the leaves, and the age of the individual leaves, in arbitrary units, is indicated by the numerals adjacent each leaf. A leaf of a suitable age is then picked, step 31. Suitable areas of the leaf are then cut into small pieces, step 32 and the pieces are placed in a tray where they are floated in an enzyme solution, for example employing one or more enzymes such as cellulase and pectinase, step 33. During step 33 the enzyme solution and the plant material are kept at a constant temperature so that protoplast is isolated gradually by removal of cell walls and the protoplast precipitates.

In step 34, the protoplast is further isolated by filtering, and the filtered protoplast 10 is placed in a suitable liquid, step 35. Then, centrifugal separation is employed, step 36, to further separate the protoplast 10. Collection treatments other than filtering and centrifugal separation may be employed for isolating the protoplast. The protoplast 10 is further cleaned and isolated by a succession of steps of washing with a liquid (step 37), removal of the liquid, (step 38), providing the protoplast 10 in a sorbitol solution (step 39), providing the protoplast with a sucrose solution (step 40) so that the protoplast will separate and collect at the interface between these liquids of different specific gravity, while waste material 61 precipitates to the bottom (step 41). In step 42, a pipette 41 or other apparatus is used to remove the protoplast and place it in another cleaning liquid, (step 43), where it precipitates and is then removed by a pipette (step 44) to complete the isolation.

The isolated protoplast is placed in a container (step 45), and then it is combined with a carrier liquid in step 46 to provide a reservoir of protoplast 10 suspended in the liquid to thereafter be placed into an injection apparatus 21 according to next step. The injection apparatus 21 will inject the protoplast and carrier liquid into the supply pool 3 adjacent the carrier plate 2 so that the protoplast may be sucked onto the carrier plate ports, step 48. After the carrier plate 2 has moved (arrow 24 of FIG. 2) into alignment with the microchamber plate 1, the protoplast is poured into the individual microchambers, step 49. In the individual microchambers, the protoplast 10 will float upwardly due to a short duration application of pressure from pressure oscillator 22 and will move downwardly due to a subsequent application of suction by the pressure oscillator 22, as indicated by the arrows, for step 50. The suction and pressure is alternately applied repeatedly by pressure oscillator 22 in step 50 to apply the above-mentioned mechanical stress.

The mechanical stress, as noted above, may be applied to the protoplast cells by the alternate provision of pressure and suction with the pressure oscillator 22 shown in FIG. 2. After a short period of time, short with respect to the prior art because of the application of mechanical stress to the cells, cell structure has changed sufficiently for accurate observation. Then the broken protoplast passes through the slits 65 of the microchambers and the survival protoplast is observed in the microchambers, step 50, to where they may be observed (step 51), for determining the viability or survivability of the cells by observing the cell form of protoplast in the microchambers, for example with the microscope 7 of FIG. 1, and thereby carrying out a cell counting operation, by an observer or by an automatic imaging, impedance measuring or other counting system.

Empirically and qualitatively, it has been ascertained that the properties of cells vary according to the following various factors. (1) Even in one plant body, the size of cells differs with the age and a portion of a leaf. (2) The survivability of cells differs according to the condition of an enzyme treatment carried out for the cell wall removing purpose. (3) When protoplast is kept in an isotonic solution having no nutriments, to prevent the cells walls from being regenerated, the viability of the protoplast lowers with the lapse of time; the present invention accelerates the influence of this factor. (4) Unsterile conditions introduce or foster foreign bodies that degrade the cells; the present invention, by reducing the time of treatment to obtain observable results, reduces or eliminates this factor.

Regarding an experimental condition with a low repeatability, it is difficult to evaluate the cell properties individually and process the results statistically. Therefore, in order to analyze the factors having influence upon the viability of cells, it is necessary to observe several hundred isolated cells under the same conditions in as short a period of time as possible. The measuring apparatus in the present invention has advantages in that it is capable of pouring a large quantity of cells into microchambers, individually, in several minutes (a short time) and quickly recognizing the form of individual cells in an isotonic solution in less than several tens of minutes (a very short time compared to the weeks or months of the prior art). The viability or survivability of cells is evaluated by observing (manually or automatically with equipment) the number of cells before and after mechanical stress has been loaded periodically on the cells in microchambers, and using the counts to determine viability. Preferably the counting is of the number of cells left in a normal shape or in an unbroken state.

Figure 4:
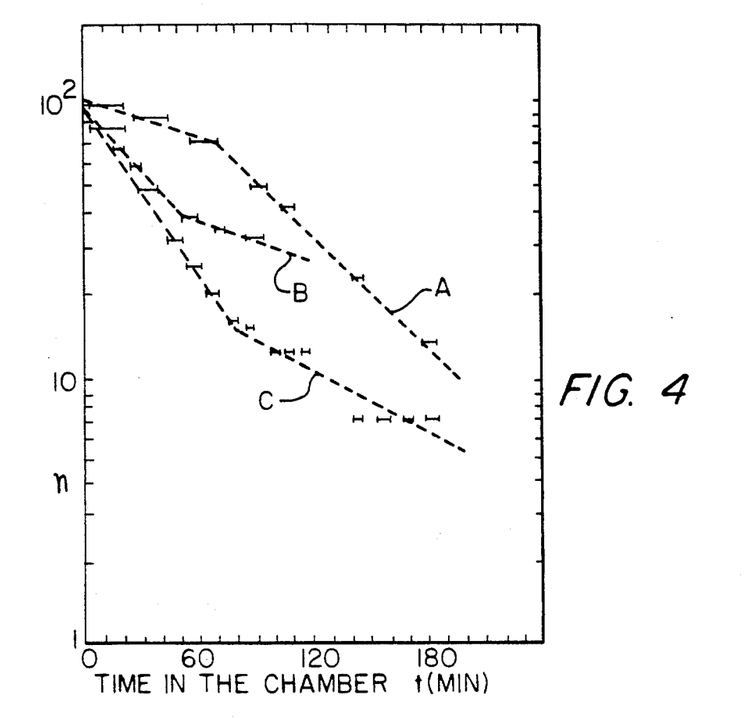
FIG. 4 is a diagram of an example of data on the basis of which the time constant of viability used in the present invention is determined.

FIG. 4 shows an example of measurements showing the condition of cell breakage and decrease of normal viable protoplast with the lapse of time. In this example, the enzyme treatment is varied as a parameter. The number of viable or survivable cells represents an average value within a measurement time, and the ranges of measurement time are shown by lateral solid lines. Broken lines A, B, and C represent regression lines of data collected respectively for protoplast wherein the enzyme pretreatment times were 0.5, 2, 4 hours. From this data, it has become clear that for each line A, B, C all the data is on the straight line portions in a semilogarithmic scale on either side of a point of inflection. Upon viewing the straight line portions, the inventors realize that an equation can be written for such straight line portions to indicate the viability, and this viability equation does not change until the inflection point is reached, a different equation would represent viability for the portion of curves, A, B, and C to the right of the inflection point. However, most advantageous results are obtained when only considering the first straight line portion of each curve A, B, C, because the viability can be quantitative in a short time, less than 60 minutes, and usually less than several 10's of minutes and thereby the parameters that produced curves, A, B, and C, respectively can be evaluated as to their affect upon viability within the short period of time, such as one hour, which is indeed quite short when compared with the conventional method requiring at least 2 to 3 weeks to determine the viability of the protoplast by allowing it to reproduce. Time 0 in FIG. 4 can be considered as the starting time immediately following the enzyme treatment, at which time the number of normal cells n0 is counted, which is then followed by mechanical stressing for a period of time up to sixty minutes sufficient to establish the straight line portion of the curve at which time the number of normal cells n is again counted, all in step 50. Accordingly, the following equation is established, in which t represents the time after the enzyme pretreatment during which the protoplast is kept in the microchambers for mechanical stressing; and n the number of normal protoplast at time t.

$$n = n_0 \cdot e^{-t/\tau} \tag{1}$$

In this equation, e is the base of the natural logarithm, $\tau$ has a dimension of time and represents the time during which cells keep their viability. Consequently, $\tau$ is defined as a time constant of viability. The variable $n_0$ is the initial number of normal cells and n is the number of normal cells after the lapse of time t.

A measuring, according to the present invention, for quantitatively determining the viability or survivability of cells will now be described. All of the protoplast cells that have been poured into the microchambers and kept in an isolated manner is subjected to the simultaneous and uniform application of a load of alternating and intermittent flotation pressure and suction pressure as mechanical stress. The microchambers positioned in a matrix form are indexed by stage scanning and observed with an optical microscope, the number of protoplast of a predetermined form, for example normal or undamaged, is counted to determine $n_0$, preferably before starting the mechanical stress. After a predetermined period of time t has passed, the interior of the microchambers is subjected to measurement again to count the number n of protoplast of the predetermined form. The time constant of viability $\tau$ is expressed by the following equation.

$$\tau = t/\ln(n_0/n) \qquad (2)$$

In this equation ln is the natural log to the base e.

Referring to the data of line C with respect to the enzyme pretreatment time of 4 hours in FIG. 4, the average number $n_0$ of normal cells counted at the time to when the pouring of protoplast has just finished, is 80, which decreases to n=20 at a point in time t which is 60 minutes later than the precedent protoplast cell counting time. Accordingly, the time constant of viability $\tau$ is 44 minutes according to the equation (2).

Referring to other data of line A with respect to the enzyme pretreatment time of 0.5 hour, $n_0$ is 96, which decreases to N=70 at a point in time t which is 55 minutes. Accordingly, the time contant of viability $\tau$ is 174 minutes.

Figure 5:
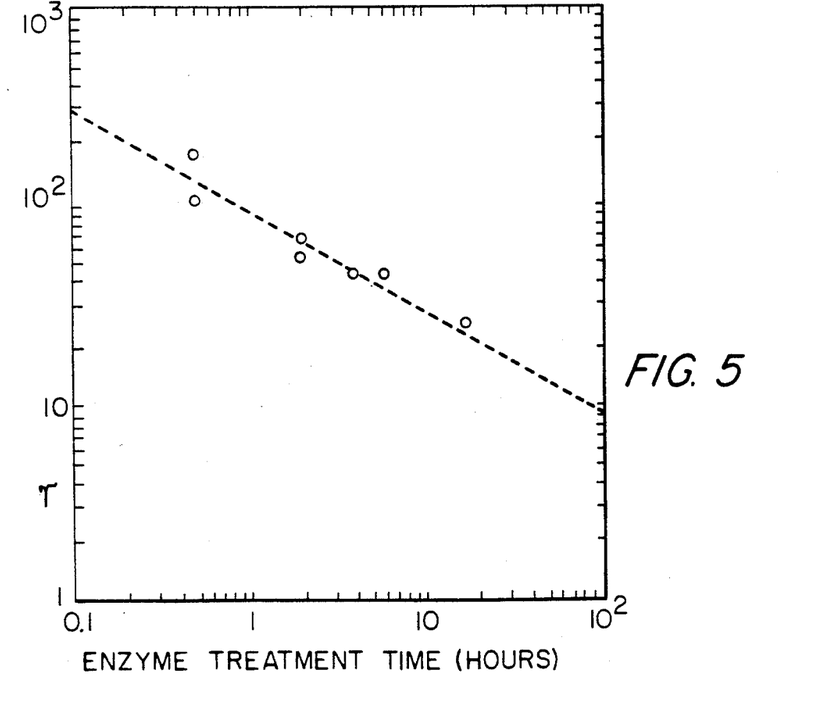
FIG. 5 is a diagram showing an example of measurement results indicating the time constant of viability (i.e. survivability, of cells) determined by the present invention relative to parameters having influence upon the viability, such as enzyme treatment time.

The time constant of viability $\tau$, which is determined as above-described according to equation (2) of the present invention with respect to different enzyme treatment times including the three treatment times of FIG. 4, is then plotted with respect to the enzyme treatment time parameter having influence upon the viability of protoplast and is shown in FIG. 5. It is noticed that, the shorter the enzyme treatment time is, the larger the time constant of viability $\tau$ becomes. If the enzyme treatment time is thus used as a parameter, the value of the time constant of viability $\tau$ with respect to the protoplast enzyme treating parameter, i.e. the treatment time, can be determined definitely and quantitatively very quickly and thus the treatment time can be quickly evaluated. Moreover, the quantitatively determined viability can be obtained in a short period of time of several ten minutes (less than one hour) as opposed to weeks or months with the prior art. This evaluation is based on quickly making clear a very small variation in protoplast viability or survivability by loading mechanical stress on the protoplast.

The parameters having influence upon the viability or survivability of protoplast include: the enzyme treatment time mentioned above, the kind of a plant in use, age of leaf, portion of tissue of the leaf, kind of enzyme solution, treatment temperature, cleaning condition, consistency of isotonic solution and condition of preservation of protoplast, and, moreover, these parameters have influence upon one another. According to the conventional techniques, protoplast is cultured under different conditions for many days with these parameters changed each time to evaluate the results, so that a great deal of labor and time is required. If the present invention is used, the quantitative determination of the number of cells of a normal form can be done in a short period of time. This enables optimum parameters to be set easily and constitutes a great advantage of the present invention.

In the mechanical stress loading of cells used in this invention, a positive pressure of 60 Pa (10 Pa roughly equals 1 mm Aq and Pa stands for pascals) is intermittently loaded on protoplast to float the protoplast by about 200 $\mu$m during a 4-second cycle (three seconds of pressure followed by one second of suction) of alternating the positive pressure with a negative suction pressure of 50 Pa. The alternating is done continuously between counting of n and $n_0$. It has been ascertained that a mechanical stress of loading a suction pressure of 50 Pa on protoplast cells, continuously, enables the variation of properties shown in FIG. 4 to be evaluated about 4 times speedier than the cyclic method with 4-second cycles.

The mechanical stress loading on the cells can be set selectively in accordance with the degree of difficulty in determining the form of the object cell, so that the time required to evaluate the variation of properties can be selectively increased and decreased. It is possible to apply mechanical stress to the cells under control of circuit 80 by applying an electrical pulse applied by a pulse generator 70 in FIG. 3, and applying low frequency or supersonic oscillation thereto by a low or high frequency generator 68 or 69 according to selector 67 and distributor 66. Alternatively mechanical stress may be applied by supersonic generator 71 of FIG. 3, or applying heating and cooling alternately to the protoplast by heating and cooling apparatus 73, 72 of FIG. 3. These may be used altogether in combination or separately. If in any case, a mechanical stress loading on the cells is for different batches of protoplast, the viability of cells can be determined relatively in quantitative terms by using a time constant of viability $\tau$.

In the present invention, an example is described in which the determination of the form of cells in the microchambers for counting n, $n_0$ is done by observing the cells with an optical microscope. This observing may employ image processing of a picture from a camera 8, such as a video camera, for determining the form of cells and use digital processing for counting the number of cells n, $n_0$ of a normal form. For the automation of the present invention, it has been experimentally proven to be effective, to provide independent electrodes 74 in FIG. 3 on both sides of the cell sucking slit 65 for each microchamber in a configuration so that a sucked cell is held therebetween. Electrical power 75 is switched to the electrodes 74 by a switching circuit 76 to measure the impedance between the electrodes and determine the form of the cell held therebetween by a measurement and control circuit 77. If the type of mechanical stress loading is changed in accordance with the cell-form determining in use, the time required to evaluate the viability of cells can be reduced.

According to a conventional method the evaluation of the viability of cells is done after the cells have been cultured for several weeks, and it is necessary that all the steps of protoplast isolating treatment be carried out under aseptic conditions for preventing the multiplication of germs during the culturing of the cells. Therefore, preparing and controlling the protoplast isolating treatment are very troublesome.

On the other hand, the evaluation according to the present invention in which mechanical stress is loaded on protoplast to determine a time constant of viability $\tau$ is capable of accelerating a decrease of the viability of cells, making phenomena clear and accurate and reducing the time required to evaluate the viability of cells to around several ten minutes. Accordingly, when only the evaluation of the viability of cells is carried out, it becomes unnecessary to take a sterilization step before the protoplast has been subjected to an isolation treatment.

Some applied examples of the present invention will now be described. The measuring apparatus according to the present invention is capable of determining the viability or survivability of cells to be measured in a short period of time by using a time constant of viability and of outputting the results. Accordingly, a treatment apparatus is provided having the functions of suitably varying parameters and conditions of a treatment liquid which have influence upon the viability of cells, and carrying out a control operation so that the time constant of viability, i.e. the viability of cells has a desired value.

When the present invention is used, parameters that provide cells of a desired, e.g. high, viability can be quickly identified and selected. Therefore, divided and multiplied cells of a high viability and cell multiplication-promoted plant bodies can be stably provided. An enzyme treatment liquid optimum for isolating protoplast with a high viability of cells to be observed can be determined quickly according to the present invention, as a specific example of using the present invention.

In the pathological field, cancerous cells are used as cells to be observed, and a suspension of an antibody or medicine as a treatment liquid parameter is used. An unknown effect of an antibody and a medicine can be evaluated quickly with a time constant of viability compared to a desired predetermined value under selected conditions for reducing the viability or survivability of cancer cells to be observed, with the present invention. This enables the development of an antibody for an anti-cancer medicine to be promoted efficiently, and a new antibody and medicine to be provided. Conversely, when useful cells are used as cells to be measured, an antibody and a medicine for increasing the time constant of viability of the useful cells can be provided easily and quickly by the present invention.

Experiments have been conducted to compare the present invention to the conventional cell evaluation. First, the present invention was evaluated as described above. The conventional processes were used by taking cells enzyme-treated in the same way as the cells treated in the example according to the present invention and placing them in the same number of microchambers and in the same manner, thereafter holding and operating the cells, additionally taking steps to insure the sterilization in the conventional method and counting the number of viable cells at intervals after picking out and cultivating. For a fixed difference in viable cells, n-n₀, the fixed difference was reached with the present invention (using mechanical stress) after several ten minutes, and reached with the evaluation of the conventional treatment after several days. Thereby, it was seen that the degradation of viability provided by the present invention was at 60 to 100 times, and sometimes 200 times faster than a corresponding degradation without the present invention. According to the present invention, the actual degradation of viability caused by the mechanical stressing must be sufficient, that is the amount of mechanical stress applied must be sufficient, to permit an evaluation of the liability after less time than the prior art could accurately predict, for example after less than 60 minutes and after less than 10 minutes, although in fact the viability could be determined at a later time if desired. It is to be understood that the placing of the cells, after some treatment, into the microchambers and periodically counting them to determine viability without mechanical stressing was only done for purposes of evaluating the present invention that includes mechanical stressing, and to the inventor's knowledge such counting and evaluation without mechanical stressing has not been done conventionally, or in the prior art.

The individual placement of the cells into corresponding microchambers for the practice of the present invention is of considerable advantage in obtaining an accurate count for both n and n₀. While the present invention may be performed with respect to a large number of cells in a single common container, this would make the counting more difficult and less accurate, because the cells move about, or would require expensive and specific apparatus.

According to the present invention, the viability or survivability of cells can be determined quantitatively with ease in a short period of time, so that the efficiency in developing the techniques for improving breeding in the biotechnological field as well as the medical treatment field can be increased.

While a preferred embodiment has been set forth along with the modifications and variations to show specific advantageous details of the present invention, further embodiments, modifications and variations are contemplated within the broader aspects of the present invention, all as set forth by the spirit and scope of the following claims.

We claim:

1. A method of testing the effect of a treatment on the viability of biological cells that are protoplasts of plant cells, comprising the steps of:

holding a plurality of the cells in a corresponding plurality of at least one hundred microchambers;

counting a number $n_0$ of the cells in the microchambers that have one of a broken and normal form indicative of viability;

treating the cells with a treatment, said treatment affecting degradation of viability of the cells, for a predetermined period of time t;

after said counting the number $n_0$ and during the time t, loading a plurality of cycles of mechanical stress on the cells sufficiently to accelerate the degradation of viability by alternating the application of hydrostatic pressurization and suction to the cells for each cycle;

after said loading and after the period of time t has elapsed, counting a number n of cells in the microchambers that have said one of the broken and normal form indicative of viability; and calculating a value as a function of the counted numbers of cells $n_0$ and n and the time t, which value is useful in evaluating the degradation of viability effect of the treatment on the cells.

2. The method according to claim 1, wherein said loading is conducted sufficiently to accelerate the degradation of viability by at least a multiple of 60.

3. The method according to claim 1, wherein no specific steps are taken to establish and maintain aseptic conditions for the cells during the predetermined period of time due to the accelerated degradation.

4. The method according to claim 1, wherein said steps of counting and loading are conducted while maintaining the cells suspended in an isotonic solution with an osmotic pressure maintained at a predetermined level during the entire period of time t.

5. The method according to claim 1, wherein said step of loading oscillates the mechanical stress at a controlled frequency during substantially the entire period of time t.

6. The method according to claim 1, wherein each of said steps is conducted substantially simultaneously and identically with respect to at least a thousand of said microchambers, each containing substantially identical quantities of cells.

7. The method according to claim 1, including a first step of enzyme treating the cells for digesting and removing cell walls prior to said steps of counting, loading, and calculating.

8. A method according to claim 7, wherein said step of enzyme treating treats with a digesting enzyme know as cellulase.

9. The method according to claim 1, wherein said step of calculating calculates a value of a time constant of viability equal to the prescribed period of time divided by the natural log of $(n_0/n)$ so that the time constant of viability becomes larger to indicate a greater degradation of viability.

10. The method according to claim 9, wherein said loading is conducted sufficiently to accelerate the degradation of viability by at least a multiple of 60.

11. The method according to claim 1, wherein said steps of counting include optically observing the cells by an electronic camera.

12. The method according to claim 1, wherein said steps of counting include detecting the electrical impedance of individual cells.

13. The method according to claim 1, wherein said function is a ratio between t and some function of $n_0$ and n.

14. The method of claim 1, including repeating all of said steps with respect to a different plurality of cells differing from the first mentioned plurality of cells by a difference in treatment parameters affecting viability; thereafter plotting the values obtained from each of said steps of calculating versus the treatment parameter by which the treatments differ; and evaluating the treatment parameter according to the plot.

15. The method of claim 1, including conducting all of said steps in a cell environment that does not promote cultivation so that the cells are not cultivated during the method.

16. The method according to claim 15, wherein said step of holding includes holding individual cells respectively in individual ones of at least 100 said microchambers, and maintaining the cells in said respective microchambers throughout said steps of counting and loading.

17. The method according to claim 16, wherein said steps of counting and calculating are conducted so that the time t is less than one hour.

18. The method according to claim 17, wherein said loading is conducted sufficiently to accelerate the degradation of viability by at least a multiple of 60; and
wherein no specific steps are taken to establish and maintain aseptic conditions for the cells during the predetermined period of time due to the accelerated degradation.

19. The method according to claim 15, wherein said steps of counting and calculating are conducted so that the time t is less than one hour.

20. The method according to claim 19, wherein said loading is conducted sufficiently to accelerate the degradation of viability by at least a multiple of 60; and
wherein no specific steps are taken to establish and maintain aseptic conditions for the cells during the predetermined period of time due to the accelerated degradation.

21. The method according to claim 15, wherein said loading is conducted sufficiently to accelerate the degradation of viability by at least a multiple of 60.

22. The method of claim 21, wherein said step of holding holds individual cells respectively in individual ones of at least 100 said microchambers, and maintaining the cells in said respective microchambers throughout said steps of counting and loading.

23. The method of claim 21, wherein said steps of counting and determining are conducted so that the time t is less than the time required to reach a point of inflection between two adjacent straight line portions of a plot of the number of survivable cells n on a logarithmic scale versus the time t.

24. The method of claim 23, wherein said steps of counting and calculating are conducted so that the time t is less than one hour.

25. The method of claim 23, wherein said step of holding holds individual cells respectively in individual ones of at least 100 said microchambers, and maintaining the cells in said respective microchambers throughout said steps of counting and loading.

26. The method according to claim 25, wherein said steps of counting and calculating are conducted so that the time t is less than one hour.

27. The method of claim 1, wherein said step of holding holds individual cells respectively in individual ones of at least 100 said microchambers, and maintaining the cells in said respective microchambers throughout said steps of counting and loading.

28. The method according to claim 27, wherein said steps of counting and calculating are conducted so that the time t is less than one hour.

29. The method according to claim 28, wherein said loading is conducted sufficiently to accelerate the degradation of viability by at least a multiple of 60; and
wherein no specific steps are taken to establish and maintain aseptic conditions for the cells during the predetermined period of time due to the accelerated degradation.

30. The method according to claim 29, wherein said step of loading repeats the mechanical stress throughout the entire period of time t.

31. The method according to claim 30, including maintaining the cells in a liquid throughout the time t so that the pressure and suction are hydrostatically applied.

32. The method of claim 1, wherein said calculating is conducted so that the value equals $t/\ln(n_0/n)$.

33. The method of claim 1, wherein said steps of counting and calculating are conducted so that the time t is less than one hour.

34. The method according to claim 33, wherein said loading is conducted sufficiently to accelerate the degradation of viability by at least a multiple of 60; and
   wherein no specific steps are taken to establish and maintain aseptic conditions for the cells during the predetermined period of time due to the accelerated degradation.

35. The method of claim 1, wherein said steps of counting and calculating are conducted to that the time t is less than the time required to reach a point of inflection between two adjacent straight line portions of a plot of the number of cells n on a logarithmic scale versus the time t.

36. The method according to claim 35, including conducting all of said steps in a cell environment that does not promote cultivation so that the cells are not cultivated during the method.

37. The method according to claim 35, wherein said step of holding holds individual cells respectively in individual one of at least 100 said microchambers, and maintaining the cells in said respective microchambers throughout said steps of counting and loading.

38. The method according to claim 35, wherein said steps of counting and calculating are conducted so that the time t is less than one hour.

39. The method according to claim 38, wherein said step of holding holds individual cells respectively in individual ones of at least 100 said microchambers, and maintaining the cells in said respective microchambers throughout said steps of counting and loading.

40. The method according to claim 1, wherein said step of loading cyclically repeats the mechanical stress throughout the entire period of time t.

41. A biological cell viability evaluation apparatus, comprising:
   means for isolating a plurality of biological cells that are protoplasts of plant cells in a corresponding plurality of microchambers for testing the affect of a treatment on degradation of viability of the cells;
   means for alternately loading hydrostatic pressure and suction cyclically over a period of time t for providing mechanical stress on the cells sufficiently to accelerate the degradation of viability of the cells;
   means for counting a number of cells $n_0$ prior to and a number of cells n after the loading by said means for loading that have one of a broken and a normal form indicative of viability; and
   means for calculating the biological viability of the cells as a function of n, $n_0$ and t.

42. The apparatus of claim 41, wherein said means for isolating includes at least 100 said microchambers, each for containing substantially identical quantities of cells and substantially identical cells.

* * * * *